(12) United States Patent
Dehnad

(10) Patent No.: US 8,728,115 B2
(45) Date of Patent: *May 20, 2014

(54) TETHERED COIL FOR TREATMENT OF BODY LUMENS

(71) Applicant: Depuy Synthes Products, LLC, Raynham, MA (US)

(72) Inventor: Houdin Dehnad, El Granada, CA (US)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/744,170

(22) Filed: Jan. 17, 2013

(65) Prior Publication Data

US 2013/0131702 A1    May 23, 2013

Related U.S. Application Data

(62) Division of application No. 13/243,744, filed on Sep. 23, 2011, now Pat. No. 8,366,738, which is a division of application No. 11/938,056, filed on Nov. 9, 2007, now Pat. No. 8,034,075.

(51) Int. Cl.
    *A61M 29/00* (2006.01)
(52) U.S. Cl.
    USPC ........................................................ 606/200
(58) Field of Classification Search
    USPC ......... 606/108, 110, 113, 127, 128, 157, 159, 606/191, 194, 198, 200; 604/104, 523, 509, 604/96.01, 907; 623/23.65, 23.75
    See application file for complete search history.

(56) References Cited

U.S. PATENT DOCUMENTS

| 4,706,671 | A | 11/1987 | Weinrib |
| 5,226,911 | A | 7/1993 | Chee et al. |
| 5,733,329 | A | 3/1998 | Wallace et al. |
| 7,055,812 | B2 | 6/2006 | Balsells |
| 2006/0036281 | A1 | 2/2006 | Patterson et al. |
| 2006/0116711 | A1 | 6/2006 | Elliott |
| 2006/0224177 | A1 | 10/2006 | Finitsis |
| 2006/0224179 | A1 | 10/2006 | Kucharczyk et al. |
| 2006/0229638 | A1 | 10/2006 | Abrams et al. |
| 2007/0016233 | A1 | 1/2007 | Ferrera et al. |
| 2008/0091223 | A1 | 4/2008 | Pokorney |

FOREIGN PATENT DOCUMENTS

| WO | 2006014491 A2 | 2/2006 |
| WO | 2006107641 A1 | 10/2006 |

OTHER PUBLICATIONS

JPO, Office Action in counterpart application JP 2010-533297 dated Feb. 26, 2013.
EPO, International Search Report for PCT International Application No. PCT/US2008/082882 dated Jan. 20, 2009.
EPO, International Preliminary Report on Patentability for PCT International Application No. PCT/US2008/082882 dated May 11, 2010.

*Primary Examiner* — Ryan Severson
*Assistant Examiner* — Katherine M Shi
(74) *Attorney, Agent, or Firm* — Fulwider Patton LLP

(57) ABSTRACT

Disclosed is an apparatus and a method for removable of undesired material from body lumens. The apparatus may be used for fragmenting or removing a thrombus or occlusion from a blood vessel. The apparatus includes first shape segments and second shape segments connected to form a coiled member. A longitudinally extending tether is positioned inside the first shape segments and outside the second shape segments along the length of the coil. Applying a proximal force on the tether produces a change in the shape of at least a portion of the coil from a first generally linear configuration to a second complex three dimensional shape. A method of using the apparatus to engage and remove, or fragment, the thrombus or occlusion is disclosed.

6 Claims, 7 Drawing Sheets

US 8,728,115 B2

TETHERED COIL FOR TREATMENT OF BODY LUMENS

CROSS-REFERENCES TO RELATED APPLICATIONS

This application is a divisional of U.S. Ser. No. 13/243,744, filed Sep. 23, 2011, now U.S. Pat. No. 8,366,738, which is a divisional of U.S. Ser. No. 11/938,056, filed Nov. 9, 2007, now U.S. Pat. No. 8,034,075, issued Oct. 11, 2011, which is incorporated by reference in its entirety.

FIELD OF THE INVENTION

The present invention relates generally to medical devices for treatment of body lumens. More specifically, the present invention relates to medical devices for fragmentation and/or removal of blood clots, emboli, or other pathology from body lumens such as blood vessels.

BACKGROUND

Medical devices and methods of treatment of an obstructed body lumen are known in the art. Such known treatments of a body lumen include increasing blood flow through an occluded blood vessel by fragmenting or retrieving a thrombosis, blood clot, or embolism located within the lumen of the blood vessel. There has been recognized by those skilled in the art a need for improved medical devices and improved methods for treating obstructed body lumens including obstructed blood vessels.

SUMMARY OF THE INVENTION

Briefly and in general terms, the present invention provides a new and improved apparatus for the treatment of a body lumen including a tethered coil device adapted for treatment of the body lumen, including a coiled member, having at least one first shape segment longitudinally connected with at least one second shape segment. The first shape segment has a first cross sectional area and the second shape segment has a second cross sectional area that is less than the first cross sectional area. The coiled member has a proximal end and a distal end, a first generally linear configuration, and a secondary generally three dimensional configuration. The device includes a tether having a distal tether portion and a proximal tether portion. The distal tether portion is connected with the coiled member of the device at an attachment point, and slidingly disposed generally longitudinally inside the lumen of the first shape segment and outside the wall of the second shape segment. The proximal tether portion extends proximally beyond the proximal end of the coiled member and is adapted for application of a proximal longitudinal force, which changes a shape of the coiled member from the first generally linear configuration to the secondary generally three dimensional configuration.

Furthermore, the present invention provides a method of treating a thrombus within a region of a blood vessel, including positioning a portion of a thrombus engaging device at the region of the blood vessel to be treated. The thrombus engaging device is formed from a plurality of first shape segments longitudinally connected with a plurality of second shape segments and further includes a tether slidingly threaded between at least one first shape segment and one second shape segment. The method further includes transforming the portion of the thrombus engaging device from a generally linear configuration to a secondary generally three dimensional configuration by applying a proximally directed force on the tether, thereby engaging the thrombus with the thrombus engaging device.

Other features and advantages of the invention will become more apparent from the following detailed description of preferred embodiments of the invention, when taken in conjunction with the accompanying exemplary drawings.

BRIEF DESCRIPTION OF THE DRAWINGS

These and other features, aspects and advantages of the present invention are described with reference to drawings of a preferred embodiment, which are intended to illustrate, but not to limit, the present invention.

DETAILED DESCRIPTION OF THE PREFERRED EMBODIMENTS

Figure 1:
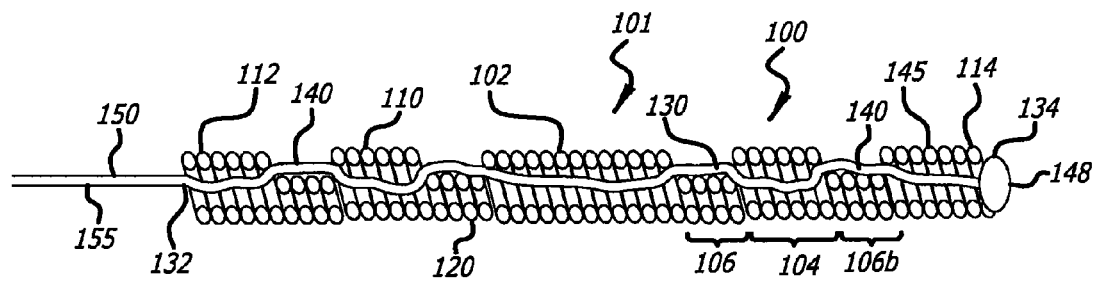
FIG. 1 is a side view of one embodiment of the body lumen treating device of the present invention in a first configuration.

Referring to the drawings, which are provided for purposes of illustration and by way of example, one embodiment of the present invention is an apparatus for treatment of a body lumen, which is illustrated in FIGS. 1-5.

In at least one embodiment, the present invention relates to an apparatus for treating intravascular obstructions such as a blood clot, thrombus, or embolism. Although the exemplary embodiments are described herein for intravascular use, those skilled in the art will recognize that the apparatus may be useful in other than vascular body lumens.

Figure 7:
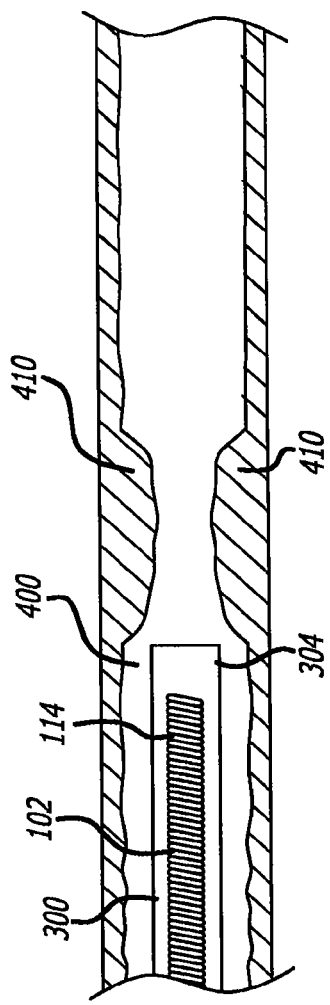
FIG. 7 is an illustration of a method of use of the body lumen treating device of FIG. 1, illustrating delivery of the device through a delivery catheter to a region of obstruction.

Referring now to FIGS. 1-3B, one embodiment of the present invention is an apparatus 100 for treatment of intravascular obstructions. The apparatus includes a coiled member 102 formed from alternating longitudinally connected segments 104 and 106, which are respectively formed primarily from first shape coil elements 110 and second shape coil elements 120. The coiled member has a proximal end 112 and a distal end 114, the distal end being adapted for positioning proximate a region to be treated, such as a thrombus or occlusion 410 (FIG. 7).

Figure 2A:
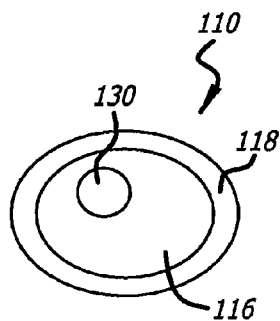
FIG. 2A is a cross sectional view through a first shape coil element of the body lumen treating device of FIG. 1.
Figure 2B:
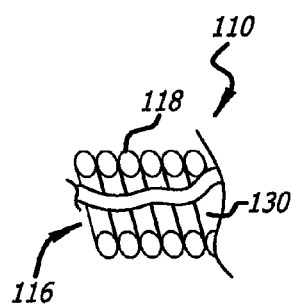
FIG. 2B is a mid-longitudinal sectional view through a portion of a first shape coil element of the body lumen treating device of FIG. 1.
Figure 2C:
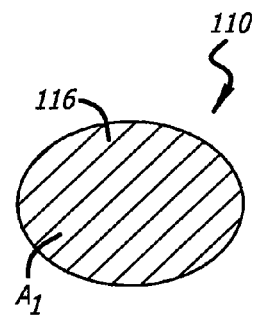
FIG. 2C is an illustration of the cross sectional area of the first shape coil element of FIG. 2A.

Referring now to FIGS. 2A-2C, in one embodiment, the invention includes first shape coil elements 110 having a generally cylindrical or ring shape, an inner lumen 116, an outer wall 118, and a cross sectional area $A_1$ defined by the outer wall. The first shape coil elements are longitudinally connected to form generally cylindrical first shape segments 104, having the cross sectional area $A_1$ and a generally helical configuration around the inner lumen 116.

Figure 3A:
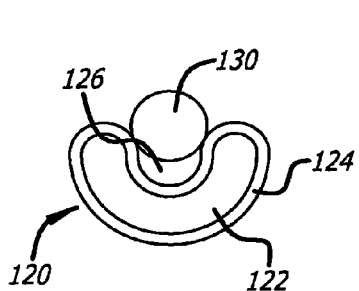
FIG. 3A is a cross sectional view through a second shape coil element of the body lumen treating device of FIG. 1.
Figure 3B:
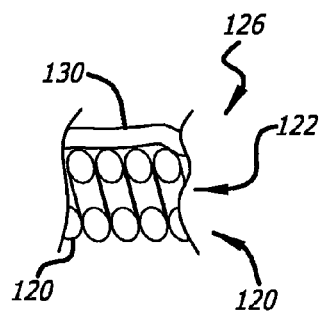
FIG. 3B is a mid-longitudinal sectional view through a portion of a second shape coil element of the body lumen treating device of FIG. 1.
Figure 3C:
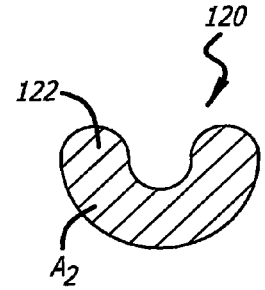
FIG. 3C is an illustration of the cross sectional area of the second shape coil element of FIG. 3A.

Referring now to FIGS. 3A-3C, in at least one embodiment the invention further includes second shape coil elements 120, which are longitudinally connected to form second shape coil segments 106. In a preferred embodiment, the second shape coil elements may have a U-shape, or horseshoe shape configuration, an inner lumen 122, an outer wall 124, an indented portion 126, and a cross sectional area $A_2$ defined by the outer wall 124. In yet other embodiments, the second shape coil segments may have other configuration and shapes. Referring more specifically now to FIGS. 2C and 3C, in one embodiment, the cross sectional area $A_1$ of the first shape coil elements 110 is greater than the cross sectional area $A_2$ of the second shape coil elements 120. In yet other embodiments, the cross sectional area $A_1$ of the first shape coil elements is less than the cross sectional area $A_2$ of the second shape coil elements. In at least one embodiment, the cross sectional shape of the first elements is different than the cross sectional shape of the second elements.

In one embodiment, at least one second shape coil segment 106 is configured to be more flexible than at least one first shape coil segment 104. Variations in flexibility of the segments 104, 106 may be provided, for example, by altering the materials, thickness, or shapes of the segments. In at least one other embodiment, at least one first shape segment is configured to be more flexible than at least one second shape segment. Furthermore, not all first shape coil segments need have the same flexibility and not all second shape coil segments need have the same flexibility.

Referring back now also to FIG. 1, the apparatus 100 of the present invention further includes a longitudinally extending tether 130, which extends generally longitudinal down the length of the apparatus 100. The term tether as used herein is not intended to be limiting and includes any number of substantially longitudinally extending members known in the art including, for example, wires, twisted wires, cables, fibers, natural fibers, polymer fibers, cords, and strings. In at least one embodiment, the tether is slidingly positioned or threaded between at least one first shape segment 104 formed from first shape elements 110 and at least one second shape segment 106 formed from second shape elements 120.

The tether 130 includes a proximal portion 150 having a free end 155, a distal portion 145 connected with the coil member 102, and an intermediate portion 140. In a preferred embodiment, the intermediate portion 140 of the tether is generally disposed inside the inner lumen 116 of the first shape segments 110 (FIGS. 2A and 2B) and outside the wall 124 of the second shape segments 120 (FIGS. 3A and 3B).

The tether 130 is connected with the coiled member 102 at at least one attachment point 134. The attachment point may be disposed on the coiled member 102 or at a distal blunt tip 148 of the device 100. The tether may be fixedly connected with the coil at the attachment point. The tether may be connected to the attachment point, for example, by glue, welding, snap fits, or friction, or by other methods well known in the art. In yet another embodiment (not shown), a distal loop in the tether may be connected with the coiled member to provide the attachment point. In at least one embodiment, the distal attachment point is located at the distal end 114 of the coiled member 102. In yet another embodiment, the blunt tip may be configured as a distal mass formed from the same materials as the tether. In at least one other embodiment the attachment point may be disposed between the distal end 114 of the coiled member 102 and the proximal end 112 of the coiled member 102. In one further embodiment, the apparatus 100 may include more than one tether and/or more than one attachment point.

The intermediate portion 140 of the tether 130 is that portion of the tether that extends longitudinally from the proximal end 112 of the coiled member 102 to the attachment point 134. In one embodiment, the tether may enter the lumen 116 of the coiled member at an entry point 132 disposed at the proximal end of the coiled member. In another embodiment, the tether may enter the lumen 116 of the coiled member at a position that is distal to the proximal end 112 of the coiled member. The tether further includes a proximal portion 150 having a free end 155. The proximal portion of the tether 150 is that portion of the tether that extends proximally from the proximal end 112 of the coiled member 102. The free end 155 and proximal portion 150 of the tether 130 are preferably configured to remain outside of the body lumen during treatment with the apparatus 100. Furthermore, the free end 155 of the tether 130 is adapted for application of a substantially longitudinal proximally directed tensioning force F by a clinician. The free end of the tether may further be connected to a handle and/or reel (not shown) configured to assist the clinician in applying a controlled longitudinal tensioning force F to the tether 130. The coiled member is configured to bend, forming an angle greater than zero at at least one first shape segment and/or at at least one second shape segment when the proximally directed tensioning force F is applied. In yet one further embodiment, the coiled member is capable of returning to a generally linear or straightened first configuration when the tensioning force F is released.

The intermediate portion of the tether 140 is generally slidingly laced or threaded between the first shape segments 104 and the second shape segments 106. In at least one embodiment, the tether slidingly extends longitudinally from the proximal end 112 towards the distal end 114 of the coiled member 102, and the tether 140 is generally disposed within the inner lumen 116 of at least one first shape segment 104 and outside the outer wall 124 of at least one second shape segments 106.

Figure 5:
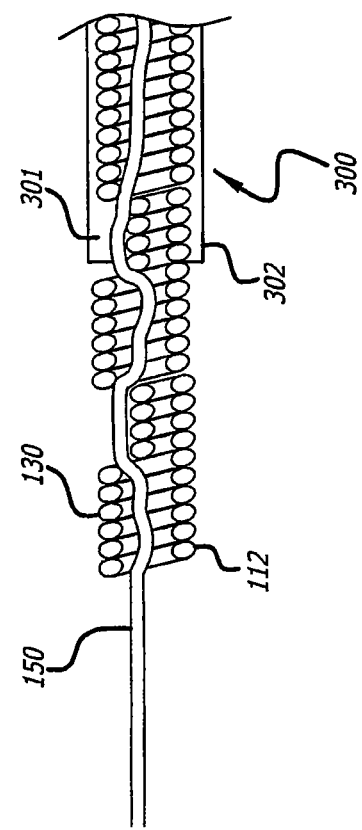
FIG. 5 is a side view of an embodiment of the body lumen treating device of the present invention further including a catheter.
Figure 5:
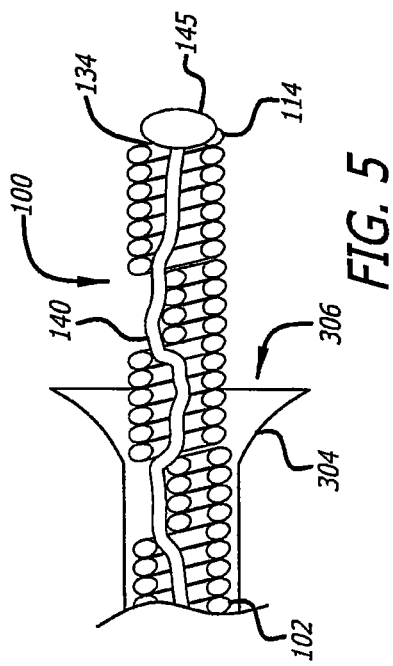

In at least one preferred embodiment, a portion of the tether 130 is slidingly disposed within the recess 126 of the second shape segment. The positioning of the tether 130 within the recess 126 of the second shape segment 120 is advantageous in providing a generally uniform outer diameter of the apparatus 100. The tether 130 is disposed such that it is closer than the outer walls 118 of the coil member to the central longitudinal axis of the device 100. This configuration provides that the tether does not extend peripherally beyond the outer walls 118 of the first shape segments 104, thereby reducing friction between the tether and the delivery catheter 300 and facilitating delivery of the apparatus through the lumen of a delivery catheter (FIG. 5).

The coiled member 102 of the apparatus 100 has a first generally linear or straightened configuration 101 (FIG. 1) in a relaxed state. Furthermore, the coiled member of the apparatus has at least one secondary generally three dimensional configuration 201, 202 (FIGS. 4A and 4B) in a tensioned state. In at least one embodiment, applying the proximally directed substantially longitudinal force F upon the tether 130 produces the transformation in shape from the relaxed or non-tensioned first generally linear configuration to at least one tensioned secondary three dimensional configuration. Applying the tensioning force F upon the tether proximal portion 150, proximally displaces a portion of the tether 130 to a position that is proximal to the proximal end 112 of the coil member. The longitudinal force F thereby effectively shortens the intermediate portion 140 of the tether 130, namely that portion that remains distal to the proximal end of the coiled member, from a length $L_1$ to a length $L_2$, wherein $L_2$ is shorter than $L_1$.

In at least one embodiment, at least one second shape segment 106 of the coiled member 102 is configured to bend, thereby creating a flexion point at the second shape segment upon tensioning of the tether 130 by proximal force F and shortening of the intermediate portion 140 of the tether 130 from a length $L_1$ to a length $L_2$. The bending or flexing at second shape segment 106 produces an angle greater than zero degrees between a first shape segment 104 and at least one other first shape segment, such as an adjacent first shape segment, thereby transitioning the coiled member to at least one secondary three dimensional configuration. In at least one other embodiment, at least one first shape segment 104 of the coiled member 102 is configured to bend, thereby creating a flexion point at the first shape segment upon tensioning of the tether 130 by proximal force F and shortening of the intermediate portion 140 of the tether 130 from a length $L_1$ to a length $L_2$. The bending or flexing at first shape segment 104 produces an angle greater than zero degrees between a second shape segment 106 and at least one other second shape segment 106b, thereby transitioning the coiled member to at least another secondary three dimensional configuration.

In one further embodiment, releasing proximal force F from the tether proximal portion 150 permits the coil 102 to return to the first generally linear configuration 101. Release of proximal force F permits the intermediate portion 140 of the tether 130 to return towards length $L_1$ from shortened length $L_2$. The coil may urged to return to the first generally linear configuration 101 by forming the coil with a preferred shape memory linear configuration, such that when the apparatus 100 is in a relaxed state, which is free of external forces applied to the tether, the coil tends to take the linear configuration. For example, the coil may be formed from materials known in the art to have shape memory properties, such as Nitinol. The coil may alternatively be formed from other materials such as biocompatible metals, alloys, and polymers. Alternatively or in addition to forming the coil with a preferred shape memory linear configuration 101, the coil may be urged into a generally linear configuration by sliding the coiled member into the lumen of a delivery catheter 300 (FIG. 5).

Figure 4A:
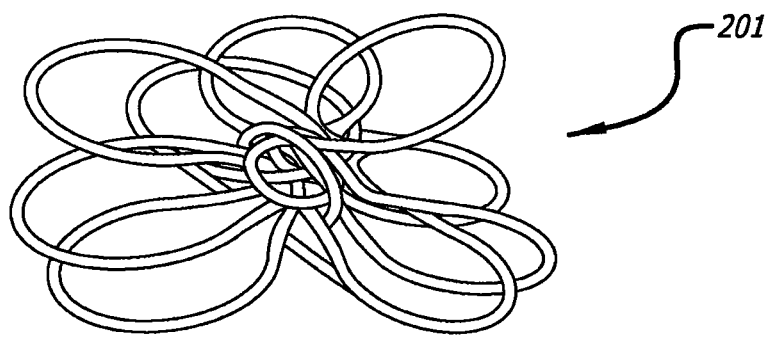
FIG. 4A is an illustration of the body lumen treating device of FIG. 1 in a second three dimensional configuration.
Figure 4B:
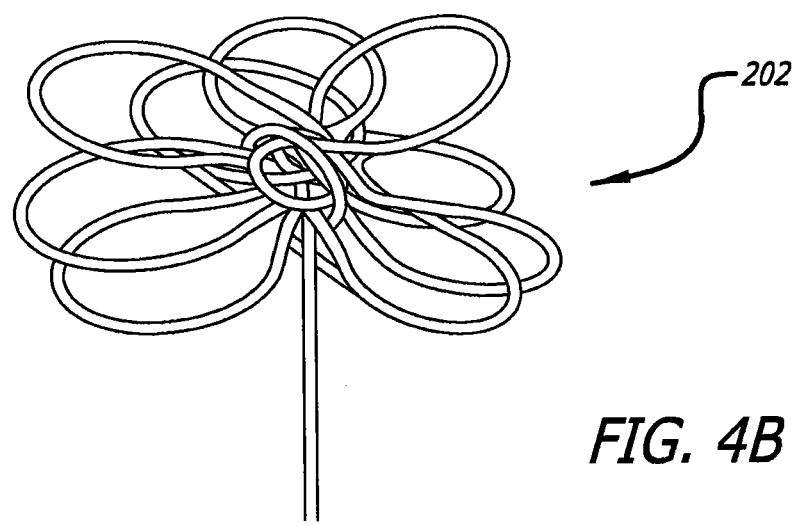
FIG. 4B is an illustration of the body lumen treating device of FIG. 1 in a second three dimensional configuration.
Figure 4C:
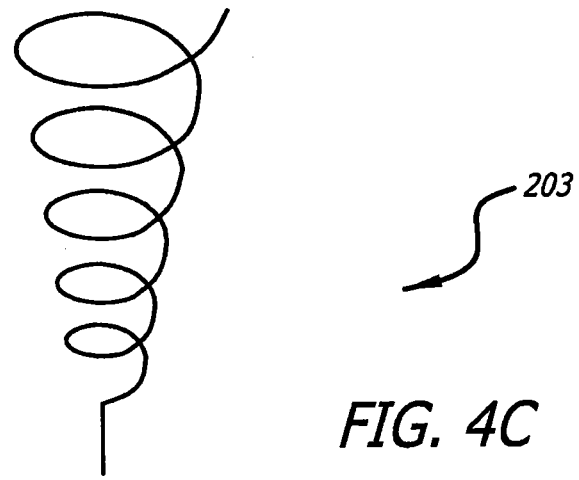
FIG. 4C is an illustration of the body lumen treating device of FIG. 1 in a second three dimensional configuration.
Figure 4D:
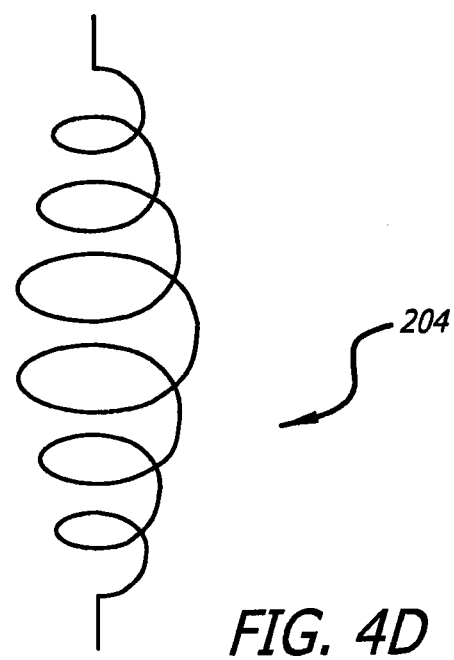
FIG. 4D is an illustration of the body lumen treating device of FIG. 1 in a second three dimensional configuration.

Various secondary three dimensional configurations 201-204 may be produced by altering such factors as the pattern of positioning of the tether 130 amongst the segments 104 and 106, the flexibility or rigidity of the first shape segments 104 or the second shape segments 106, the number of first shape elements 110 or second shape elements 120 per segment 104, 106, the attachment location 134 of the tether to the coil 102, the amount and duration of the proximal longitudinal force F on the tether, and the frictional forces between the tether and the coil. A few examples of secondary three dimensional configurations are illustrated in FIGS. 4A-4D, however, those skilled in the art will recognize that multiple other three dimensional configurations are possible. One such example of a secondary complex three dimensional configuration is a flower petal configuration 201 (FIG. 4A). Another example of a secondary complex three dimensional configuration is a globular configuration 202 (FIG. 4B). Yet another example of a secondary complex three dimensional configuration is a helical configuration 203 (FIG. 4C). Still another example of a secondary complex three dimensional configuration is a beehive configuration 204 (FIG. 4D). A multitude of secondary three dimensional configurations may be provided by variation in several apparatus factors. One such factor is variation in the location of at least one attachment point 134. Another such factor is the number of tethers 130. Still another factor is the location of the first shape segments and the second shape segments. Yet another factor is the length of the first shape segments and the length of the second shape segments. Another exemplary factor is the flexibility of the first shape segments and the flexibility of the second shape segments. A further factor is the angle of the helical turns of the first shape segments and the second shape segments. The secondary three dimensional configuration shapes illustrated and described herein are therefore meant to only be by way of example and not limiting as to the various numbers, locations, and angles of one or more bends that that can configured along the length of the coil, thereby resulting in a plurality of secondary three dimensional shapes.

Referring now to FIG. 5, at least one other embodiment of the apparatus 100 further includes a delivery catheter 300 having a proximal end 302, a distal end 304, and a lumen 301 therebetween. The distal end of the catheter is configured to be delivered into a body lumen, such as a blood vessel, and advanced to the portion of the body lumen to be treated. In at least one embodiment, distal end 304 of the catheter may be configured with an enlarged or enlargeable opening 306 for receiving obstructing matter therein when such obstructing matter is retrieved by the coiled member 102. In one embodiment, coiled member 102 is longer than the delivery catheter 300, such that during clinical use the proximal end 112 of the coiled member and the proximal portion of the tether 150 remains outside the catheter and the body lumen, wherein the coiled member and the tether and may be manipulated by the clinician for treatment of a patient.

In at least one embodiment, the apparatus 100 may be configured such that the catheter 300 is relatively rigid, thereby resisting deformation or bending of the catheter when the coiled member 102 is transformed from the first linear configuration 101 to the secondary three dimensional configurations 201. Therefore, in one embodiment, only the portion of the coil that extends distally from the distal end of the catheter will assume the secondary three dimensional configuration when tensioning force F is applied to the proximal tether 150. In yet another embodiment, the apparatus 100 is configured such that a portion of the catheter is flexible, wherein when the coiled member is transitioned from the first linear configuration 101 towards the secondary three dimensional configurations 201 by force F, the clinician can steer a portion of the catheter. The clinician may apply varying amounts of force F to the proximal tether 150, thereby directing a portion of the catheter in a desired direction within the body lumen.

Figure 6:
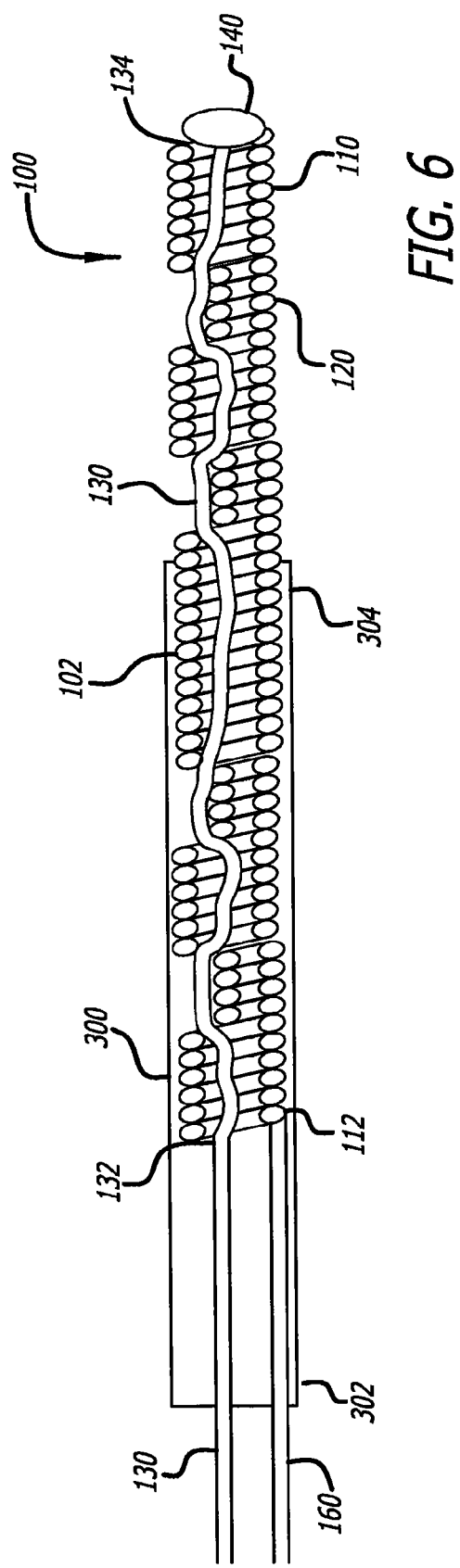
FIG. 6 is a side view of an embodiment of the body lumen treating device of the present invention further including a catheter and a delivery member.

Referring now to FIG. 6, in yet another embodiment of the apparatus 100, a delivery member 160 is connected to the proximal end of the coiled member 102. In such an embodiment, the proximal end 112 of the coiled member may be disposed within the catheter, but controlled by the clinician from outside the body lumen by manipulating the delivery member. The proximal portion of the tether 150, remains outside the catheter and may be manipulated by the clinician to apply tensioning force F.

Referring now to FIGS. 7-10, one further embodiment of the present invention includes a method of treatment of an occlusion of a body lumen utilizing the apparatus 100. Although in the exemplary method described herein the body lumen is a blood vessel, the method is applicable to removal of undesired material from other lumens. The method may include treatment of a total occlusion of a blood vessel or treatment of a partial occlusion of a blood vessel.

In one embodiment, the method of treatment includes percutaneously inserting the delivery catheter 300 into a blood vessel lumen, such as an artery lumen. The distal end 304 of the catheter is positioned, for example using well known interventional radiology techniques, to a location in the body lumen 400 adjacent to a region of thrombus or occlusion 410. The distal end 304 of the catheter may be positioned proximal to the thrombus or occlusion. In yet another embodiment, the distal end of the catheter may be advanced into and/or beyond the region of thrombus or occlusion. As is well known in the art, the proximal end 302 (FIGS. 5 and 6) of the catheter preferably remains outside the body lumen for manipulation by the clinician. The coiled member 102 of the tethered coil apparatus 100 in the first generally linear configuration 101 (FIG. 1), in the relaxed state, may be delivered through the lumen 301 of the delivery catheter, adjacent to the region of thrombus or occlusion. In the first generally linear configuration, the intermediate portion 140 of the tether 130 has a relaxed length $L_1$ (FIGS. 1 and 5).

Figure 8:
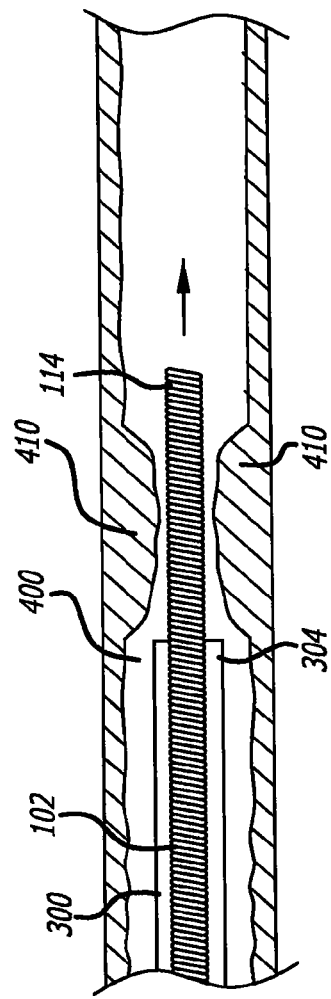
FIG. 8 is an illustration of the method of use of FIG. 7, further illustrating delivery of the device through the obstruction.

Referring more specifically now to FIG. 8, the distal end 114 of the coiled member 102 may be advanced through the delivery catheter 300 and body lumen 400 into and/or beyond the region of thrombus or occlusion 410. The distal end 114 of the coiled member may be advanced distally beyond the distal end of the delivery catheter. In one further embodiment, the distal end 304 of the catheter may be expanded to form an enlarged opening 306 for receiving the thrombus or occlusion after it has been engaged by the coiled member.

Figure 9:
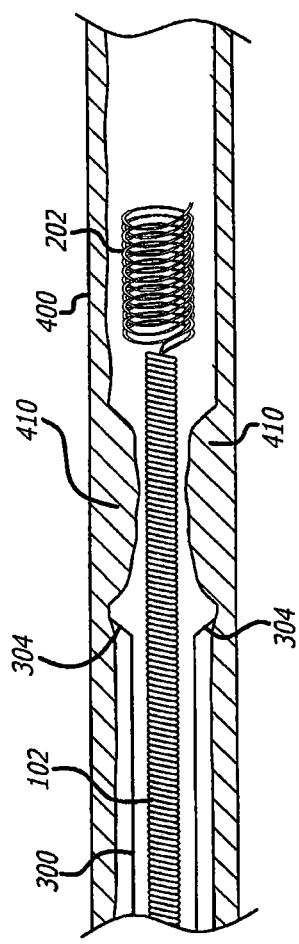
FIG. 9 is an illustration of the method of use of FIG. 7, further illustrating delivery of the device through the obstruction. further illustrating expanding the device to a secondary three dimensional configuration.

Referring now to FIG. 9, the coiled member 102 may be transitioned into a tensioned state by applying tensioning force F to the tether 150, thereby forming at least one secondary complex three dimensional configuration 201-204 (FIGS. 4A-4D). The coiled member 102 may be transitioned into a tensioned state by the clinician apply proximal longitudinal force F (FIG. 1) upon the proximal portion 150 of the tether 130, thereby shortening the intermediate portion 140 of the tether to tensioned length L2. The coil in the secondary three dimensional configuration may be used to engage or fragment the thrombus or occlusion 401.

Figure 10:
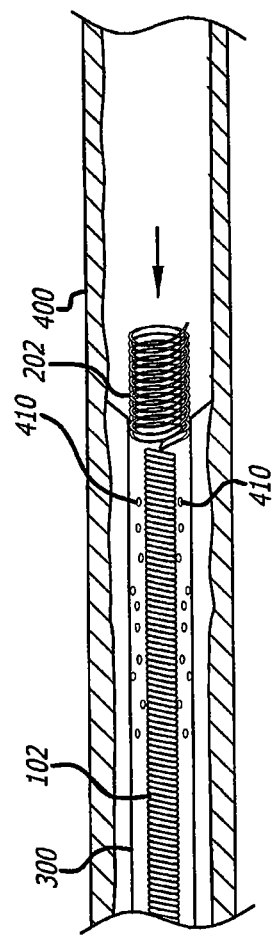
FIG. 10 is an illustration of the method of use of FIG. 7, further illustrating withdrawing the device through the obstruction. and into the delivery catheter to remove the obstruction.

Referring to FIG. 10, the coiled member 102 in the secondary three dimensional configuration may be used to engage the thrombus or occlusion and deliver it into the distal end 304 or enlarged opening 306 of the delivery catheter 300 for removal from the body lumen 400. The method may include using more than one type of secondary three dimensional configuration during the procedure. The available secondary three dimensional configurations may be predetermined, for example, by selecting from the apparatus factors discussed above. The secondary three dimensional configurations for the apparatus may also be varied by the clinician during the procedure by selecting the amount and/or duration of proximal longitudinal force F on the tether 150 and/or by varying the amount of shortening from $L_1$ to $L_2$.

Figure 11:
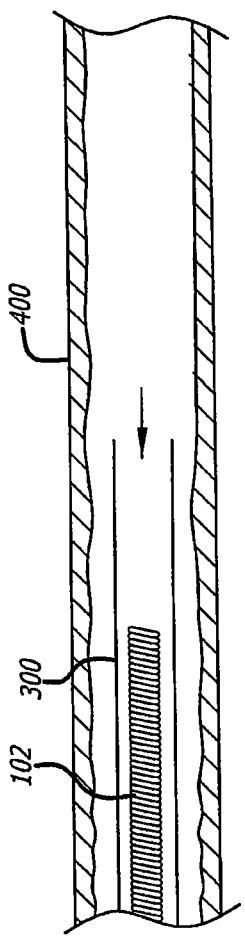
FIG. 11 is an illustration of the method of use of FIG. 7, further illustrating withdrawing the device and the delivery catheter from the body lumen.

Referring finally to FIG. 11, after the occlusion or thrombus 410 has been engaged, fragmented, and/or removed from the blood vessel 400, the coiled member 102 is returned to the first generally linear configuration 101 by releasing the tensioning force F from the tether 150, and/or by pulling the coiled member proximally into the lumen of the catheter 300 to straighten the coiled member.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

I claim:

1. An intravascular device adapted for treatment of a vascular occlusion, comprising:
a coiled member formed from a plurality of first shape coil segments alternatingly longitudinally connected with a plurality of second shape coil segments, the first shape coil segments having an inner lumen and a first cross sectional shape, and the second shape coil segments having an inner lumen and a second cross sectional shape that is different from said first cross sectional shape, the coiled member having a first generally linear configuration and a secondary complex three dimensional configuration; and
a tether having a distal tether portion connected to the coiled member at an attachment point, an intermediate tether portion slidingly disposed generally longitudinally inside the inner lumen of at least one of said plurality of first shape coil segments and outside the inner lumen of at least one of said plurality of second shape coil segments, and a proximal tether portion extending proximally beyond a proximal end of the coiled member, said tether being configured to cause said coiled member to change from said first generally linear configuration to said secondary complex three dimensional configuration upon tensioning of said tether by application of a proximal longitudinal force to said tether.

2. The intravascular device of claim 1, wherein said first cross sectional shape is generally cylindrical.

3. The intravascular device of claim 1, wherein said second cross sectional area is U-shaped.

4. The intravascular device of claim 1, wherein the attachment point is disposed at a distal end of the coiled member.

5. The intravascular device of claim 1, wherein the attachment point is disposed between the proximal end of the coiled member and a distal end of the coiled member.

6. The intravascular device of claim 1, wherein the first shape coil segments and the second shape coil segments have different flexibilities.

* * * * *